(12) United States Patent
Holmberg (10) Patent No.: US 12,161,393 B2
(45) Date of Patent: Dec. 10, 2024

(54) FORCE SENSING CATHETER SYSTEM

(71) Applicant: St. Jude Medical International Holding S.á r.l., Luxembourg (LU)

(72) Inventor: James Holmberg, Champlin, MN (US)

(73) Assignee: St. Jude Medical International Holding S.á r.l., Luxembourg (LU)

( * ) Notice: Subject to any disclaimer, the term of this patent is extended or adjusted under 35 U.S.C. 154(b) by 1102 days.

(21) Appl. No.: 16/979,837

(22) PCT Filed: Mar. 4, 2019

(86) PCT No.: PCT/IB2019/051736
§ 371 (c)(1),
(2) Date: Sep. 10, 2020

(87) PCT Pub. No.: WO2019/175706
PCT Pub. Date: Sep. 19, 2019

(65) Prior Publication Data
US 2021/0052320 A1    Feb. 25, 2021

Related U.S. Application Data

(60) Provisional application No. 62/642,178, filed on Mar. 13, 2018.

(51) Int. Cl.
*A61B 18/14* (2006.01)
*A61B 18/00* (2006.01)
*A61B 90/00* (2016.01)

(52) U.S. Cl.
CPC .......... *A61B 18/1492* (2013.01); *A61B 90/06* (2016.02); *A61B 2018/00351* (2013.01); *A61B 2018/00577* (2013.01); *A61B 2018/00773* (2013.01); *A61B 2090/065* (2016.02); *A61B 2218/002* (2013.01)

(58) Field of Classification Search
CPC .. A61B 2018/00904; A61B 2090/0064; A61B 2090/0065
See application file for complete search history.

(56) References Cited

U.S. PATENT DOCUMENTS

| 8,048,063 B2 * | 11/2011 | Aeby .................. A61B 5/6885 |
| | | 606/1 |
| 8,567,265 B2 | 10/2013 | Aeby et al. |
| 2008/0275428 A1 | 11/2008 | Tegg et al. |
| 2008/0294144 A1 * | 11/2008 | Leo ...................... A61B 5/6885 |
| | | 604/535 |
| 2017/0319269 A1 | 11/2017 | Buesseler et al. |
| 2017/0354467 A1 | 12/2017 | Rankin et al. |
| 2019/0038228 A1 | 2/2019 | Daly et al. |
| 2020/0093396 A1 | 3/2020 | Romoscanu |

FOREIGN PATENT DOCUMENTS

EP    2338430 A1    6/2010

* cited by examiner

*Primary Examiner* — Ronald Hupczey, Jr.
(74) *Attorney, Agent, or Firm* — Armstrong Teasdale LLP (57) ABSTRACT

Aspects of the present disclosure are directed toward systems and methods for detecting force applied to a distal tip of a medical catheter. In some embodiments, a medical catheter with a deformable body near a distal tip of the catheter deforms in response to a force applied at the distal tip, and a force sensor detects various components of the deformation. Processor circuitry may then, based on the detected components of the deformation, determine a force applied to the distal tip of the catheter.

14 Claims, 7 Drawing Sheets

FORCE SENSING CATHETER SYSTEM

CROSS-REFERENCE TO RELATED APPLICATIONS

This application claims priority to U.S. provisional application No. 62/642,178, filed 13 Mar. 2018, which is hereby incorporated by reference as though fully set forth herein.

BACKGROUND a. Field

The instant disclosure relates to various types of medical catheters, in particular catheters for diagnostics within, and/or treatment of, a patient's cardiovascular system. In one embodiment, the instant disclosure relates to an ablation catheter for treating cardiac arrhythmias within a cardiac muscle. More specifically, the instant disclosure relates to force sensing systems capable of determining a force applied at a distal tip of a catheter.

b. Background Art

Exploration and treatment of various organs or vessels has been made possible using catheter-based diagnostic and treatment systems. These catheters may be introduced through a vessel leading to the cavity of the organ to be explored, and/or treated. Alternatively, the catheter may be introduced directly through an incision made in the wall of the organ. In this manner, the patient avoids the trauma and extended recuperation times typically associated with open surgical procedures.

The human heart routinely experiences electrical currents traversing its many layers of tissue. Just prior to each heart contraction, the heart depolarizes and repolarizes as electrical currents spread across the heart. In healthy hearts, the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic.

Catheters are used in a variety of diagnostic and/or therapeutic medical procedures to diagnose and correct conditions such as atrial arrhythmia. Typically, in such a procedure, a catheter is manipulated through a patient's vasculature to the patient's heart carrying one or more end effectors which may be used for mapping, ablation, diagnosis, or other treatment. Where an ablation therapy is desired to alleviate symptoms including atrial arrhythmia, an ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, and high-intensity focused ultrasound. Ablation therapies often require precise positioning of the ablation catheter, as well as precise pressure exertion for optimal ablative-energy transfer into the targeted myocardial tissue. Excess pressure between the ablation catheter tip and the targeted myocardial tissue may result in excessive ablation which may permanently damage the cardiac muscle and/or surrounding nerves. When the contact pressure between the ablation catheter tip and the targeted myocardial tissue is below a target pressure, the efficacy of the ablation therapy may be reduced. Existing catheter-based force sensing systems often don't have the ability to accurately sense the load applied to the distal tip of the catheter.

Ablation therapies are often delivered by making a number of individual ablations in a controlled fashion in order to form a lesion line. To improve conformity of the individual ablations along the lesion line, it is desirable to precisely control the position at which the individual ablations are conducted, the ablation period, and the contact pressure between the ablation catheter tip and the targeted tissue. All of these factors affect the conformity of the resulting lesion line. Catheter localization systems, in conjunction with mapping systems, have vastly improved a clinician's ability to precisely position the ablation catheter tip for an ablation.

Mapping systems often rely on manual feedback of the catheter and/or impedance measurements to determine when the catheter is properly positioned in a vessel or organ. Mapping systems do not consider contact force with the vessel or organ wall that may modify the true wall location. Accordingly, the mapping may be inaccurate due to artifacts created due to excessive contact forces between the catheter and vessel/organ wall.

To facilitate improved mapping, it is desirable to detect and monitor contact forces between a catheter tip and a wall of an organ/vessel to permit more accurate mapping.

In view of the foregoing, it would be desirable to provide a catheter-based diagnostic or treatment system that permits sensing of the load applied to the distal extremity of the catheter.

The foregoing discussion is intended only to illustrate the present field and should not be taken as a disavowal of claim scope.

BRIEF SUMMARY

The instant disclosure relates to various types of medical catheters. More specifically, the instant disclosure relates to electrophysiology catheters including a deformable body for accurately detecting a force exerted on a distal tip of the catheter.

Aspects of the present disclosure are directed toward systems and methods for detecting force applied to a distal tip of a medical catheter using a fiber-optic force sensor and processor circuitry. In particular, the instant disclosure relates to a deformable body near a distal tip of a medical catheter that deforms in response to a force applied at the distal tip. The fiber-optic force sensor detects various components of the deformation, and the processor circuitry, based on the detected components of the deformation, determines a force applied to the distal tip of the catheter. In some more specific embodiments, the processor circuitry further determines a force vector based on the detected components of the deformation.

One embodiment of the present disclosure is directed to a force-sensing catheter system including a catheter tip, and a deformable body. The deformable body includes a structural member and a manifold. The structural member is coupled to the catheter tip and a lumen that extends along a longitudinal axis of the force-sensing catheter system. The structural member deforms in response to a force exerted on the catheter tip. The manifold extends through the lumen of the structural member, and is coupled to the catheter tip and a proximal end of the structural member. The manifold transmits a portion of the force exerted on the catheter tip proximally by bypassing the structural member. In some more specific embodiments, the deformable body further includes a tip base coupling the catheter tip to the manifold.

The tip base has an annular shape with inner and outer surfaces. The outer surface is circumferentially coupled to the deformable body and the inner surface is circumferentially coupled to the manifold. The tip base transmits a portion of the force exerted on the catheter tip to the manifold.

Consistent with various embodiments of the present disclosure, an ablation catheter tip assembly may include a distal tip that delivers energy to contacted tissue and a deformable body mechanically coupled to a proximal end of the distal tip. The deformable body includes a structural member that deforms in response to a force exerted on the distal tip. The structural member includes a lumen that extends along a longitudinal axis of the ablation catheter assembly. The deformable body further includes a manifold that extends through the lumen of the structural member and is mechanically coupled to the proximal end of the distal tip. The manifold limits deformation of the structural member in response to the force exerted on the distal tip by absorbing a portion of the force. In some specific implementations, the deformable body further includes a tip base having an annular shape with inner and outer surfaces. The outer surface is circumferentially coupled to the deformable body and the inner surface is circumferentially coupled to the manifold. The tip base is configured to transmit a portion of the force exerted on the catheter tip to the manifold.

In yet other embodiments, a deformable body for an intravascular catheter is disclosed. The deformable body for an intravascular catheter includes a tip adapter, a proximal body, and an axial spring. The tip adapter includes a lumen that extends through a length of the tip adapter, the tip adapter receives lateral and axial force components of a force exerted on a distal tip of the intravascular catheter. The proximal body is coaxially aligned with and slidably affixed to the tip adapter along a longitudinal axis, and absorbs a first portion of the lateral force component exerted on the distal tip. The axial spring is coaxially aligned with the tip adapter and the proximal body. A distal portion of the axial spring is mechanically coupled to the tip adapter and a proximal portion of the axial spring is mechanically coupled to the proximal body. The axial spring receives the axial force component and a second portion of the lateral component, and deforms in response to the second portion of the lateral component and the axial component of the force exerted on the distal tip. In some specific implementations, the deformable body further includes a measurement system positioned between the proximal body and the tip adapter. The measurement system includes three or more sensing elements that measure a change in relative, longitudinal position between the proximal body and the tip adapter in response to the deformation of the axial spring.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which.

While various embodiments discussed herein are amenable to modifications and alternative forms, aspects thereof have been shown by way of example in the drawings and will be described in further detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION OF EMBODIMENTS

Aspects of the present disclosure are directed toward systems and methods for detecting force applied to a distal tip of a medical catheter. In particular, the instant disclosure relates to a deformable body near a distal tip of a medical catheter that deforms in response to a force applied at the distal tip. Sensors, such as fiber-optic sensors, detect various components of the deformation, and processor circuitry, based on the detected components of the deformation, determines the force applied to the distal tip of the catheter. Importantly, various aspects of the present disclosure are directed to electrophysiology catheters including a deformable body with a tunable trans-axial/axial compliance ratio.

Various aspects of the present disclosure are directed toward a deformable body with independent axial and lateral stiffness. This deformable body may be installed within an intravascular catheter, and the deformation of the deformable body, in response to a distal tip of the catheter contacting tissue, may be measured to determine contact and/or force exerted on the distal tip. In various embodiments, the axial and lateral stiffness of the deformable body may be tunable to facilitate desired affects. For example, the deformable body may be tuned in such a way as to facilitate a 1:1 ratio (or approaching a 1:1 ratio) between axial and lateral (trans-axial) deformation.

Optical force sensing systems are commonly used in conjunction with a deformable body within an intravascular catheter to provide a clinician with additional distal tip feedback during administration of a therapy or diagnostic procedure, for example. However, existing deformable bodies suffer from lateral force sensitivity bias. That is, a lateral force exerted on the distal tip of the catheter causes a much larger deflection at the deformable body than a comparable axial force (e.g., 7-13 times). The optical force sensing system will then calculate a much higher force for lateral forces then for radial forces, resulting in high force accuracy errors. The force sensing systems may also be susceptible to thermal sensitivity which further exacerbates force accuracy errors. Aspects of the present disclosure reduce the difference between axial and lateral sensitivity of a deformable body by separating the axial and lateral stiffness components of the deformable body into independently adjustable parts. Each stiffness component may then be adjusted as desired for a given application.

Various embodiments of the present disclosure are directed to a deformable body for a catheter force sensing system. Force sensing systems as disclosed herein may be calibrated to measure forces exerted on a distal tip of a medical catheter via fiber optic measurement of a deformation of the deformable body. Such a force sensing system may be particularly useful for cardiovascular ablation catheters, where a distal tip of the catheter is positioned in contact with myocardial tissue that is to receive an ablation therapy and necrose in response to the treatment. Ablation therapy can be a useful treatment for patients with a cardiac arrhythmia (e.g., atrial fibrillation). The necrosed tissue facilitates electrical isolation of unwanted electrical impulses (arrhythmic foci) often emanating from pulmonary veins. By electrically isolating the foci from the left atrium of the cardiac muscle, for example, the symptoms of atrial fibrillation can be reduced or eliminated. To the extent that arrhythmic foci are located within a tissue ablation zone, the arrhythmic foci are destroyed.

In a typical ablation therapy for atrial fibrillation, pulmonary veins are treated in accordance to their likelihood of having arrhythmic foci. Often, all pulmonary veins are treated. A distal tip of the catheter may include electrophysiology electrodes (also referred to as spot electrodes) which help to expedite diagnosis and treatment of a source of a cardiac arrhythmia, and may also be used to confirm a successful ablation therapy by determining the isolation of the arrhythmic foci from the left atrium, for example, or the destruction of the arrhythmic foci entirely.

During an ablation therapy, a distal end of an ablation catheter tip contacts ablation targeted myocardial tissue in order to conductively transfer energy (e.g., radio-frequency, thermal, etc.) thereto. It has been discovered that consistent force, during a series of tissue ablations, forms a more uniform and transmural lesion line. Such uniform lesion lines have been found to better isolate the electrical impulses produced by arrhythmic foci, thereby improving the overall efficacy of the ablation therapy. To achieve such consistent force, aspects of the present disclosure utilize a deformable body in the ablation catheter tip. The deformable body deforms in response to forces being exerted upon a distal end of the ablation catheter tip. The deformation of the deformable body may then be measured by a measurement device (e.g., ultrasonic, magnetic, optical, interferometry, etc.). Based on the tuning of the deformable body and/or the calibration of the measurement device, the deformation can then be associated with a force exerted on the distal end of the ablation catheter tip (e.g., via a lookup table, formula(s), calibration matrix, etc.). The measurement device and/or processor circuitry may be used to determine the exerted force, and output a signal indicative of the force exerted on the catheter tip. The calculated force may then be displayed to a clinician, stored in memory, or otherwise communicated. For example, haptic feedback can be utilized in the catheter handle to indicate proper or insufficient contact force with the targeted myocardial tissue. In some specific embodiments, the processor circuitry may intervene in the ablation therapy where the force exerted on the tissue by the catheter tip is too low or too high.

Further aspects of the present disclosure are directed to a stiffened deformable body capable of handling higher load forces. During insertion of the catheter through an introducer, and/or while traveling through the vasculature of a patient, the distal tip of the catheter (and therefore the deformable body by virtue of the mechanical coupling of the two components) may experience large forces. In some applications, the deformable body may experience forces up to 1,000 grams. In various embodiments, the deformable body includes a manifold that acts in conjunction with a structural member of the deformable body to absorb such excess forces and prevent plastic deformation of the structural member. Plastic deformation is particular problematic for catheter-based force sensing applications, as the new set of the structural member renders the factory calibration of the force sensing system inaccurate. Due to such plastic deformation, when the catheter is in a non-contact position with the cardiovascular system of a patient, the force sensing system may return a force indicative of contact between the distal tip and tissue.

In one embodiment, the deformable body is tuned so that the axial compliance of the deformable body in response to a first force exerted co-axially with the ablation catheter tip is equal to the trans-axial compliance of the deformable body in response to the first force exerted trans-axial with the ablation catheter tip. Tuning the deformable body to a trans-axial/axial compliance ratio of approximately 1:1 (5:1-1:1) provides a number of important benefits. For example, during operation, the ablation catheter tip is able to precisely determine the force exerted on the catheter tip regardless of the directionality of the force. Without this linear relationship between the axial and trans-axial compliance of the deformable body, the calculated force related error would vary widely depending on the directionality of the force.

Details of the various embodiments of the present disclosure are described below with specific reference to the figures.

Figure 1:
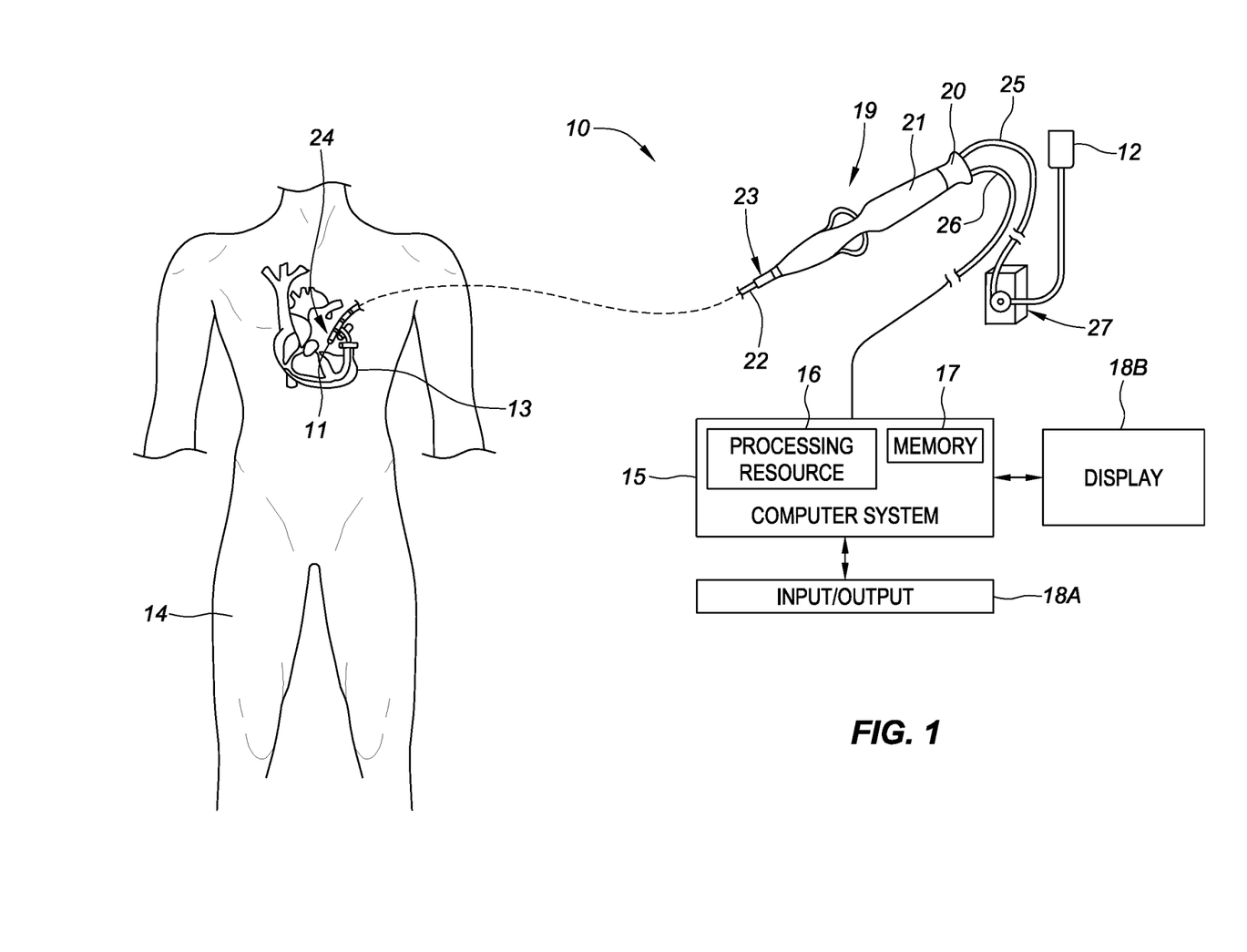
FIG. 1 is a diagrammatic overview of a system for force sensing, consistent with various embodiments of the present disclosure.

Referring now to the drawings wherein like reference numerals are used to identify identical components in the various views, FIG. 1 generally illustrates a system 10 for force detecting having an elongated medical device 19 that includes a sensor assembly 11 (e.g., fiber optic based distance measurement sensor) configured to be used in the body for medical procedures. The elongated medical device 19 may be used for diagnosis, visualization, and/or treatment of tissue 13 (such as cardiac or other tissue) in the body. For example, the medical device 19 may be used for ablation therapy of tissue 13 or mapping purposes in a patient's body 14. FIG. 1 further shows various sub-systems included in the overall system 10. The system 10 may include a main computer system 15 (including an electronic control unit 16 and data storage 17, e.g., memory). The computer system 15 may further include conventional interface components, such as various user input/output mechanisms 18A and a display 18B, among other components. Information provided by the sensor assembly 11 may be processed by the computer system 15 and may provide data to the clinician via the input/output mechanisms 18A and/or the display 18B, or in other ways as described herein. Specifically, the display 18B may visually communicate a force exerted on the elongated medical device 19—where the force exerted on the elongated medical device 19 is detected in the form of a deformation of at least a portion of the elongated medical device by the sensor assembly 11, and the measured deformations are processed by the computer system 15 to determine the force exerted.

In the illustrative embodiment of FIG. 1, the elongated medical device 19 may include a cable connector or interface 20, a handle 21, a tubular body or shaft 22 having a proximal end 23 and a distal end 24. The elongated medical device 19 may also include other conventional components not illustrated herein, such as a temperature sensor, additional electrodes, and corresponding conductors or leads. The connector 20 may provide mechanical, fluid and/or electrical connections for cables 25, 26 extending from a fluid reservoir 12 and a pump 27 and the computer system 15, respectively. The connector 20 may comprise conventional components known in the art and, as shown, may be disposed at the proximal end of the elongated medical device 19.

The handle 21 provides a portion for a user to grasp or hold the elongated medical device 19 and may further provide a mechanism for steering or guiding the shaft 22 within the patient's body 14. For example, the handle 21 may include a mechanism configured to change the tension on a pull-wire extending through the elongated medical device 19 to the distal end 24 of the shaft 22 or some other mechanism to steer the shaft 22. The handle 21 may be conventional in the art, and it will be understood that the configuration of the handle 21 may vary. In an embodiment, the handle 21 may be configured to provide visual, auditory, tactile and/or other feedback to a user based on information received from the sensor assembly 11. For example, if contact to tissue 13 is made by distal tip 24, the sensor assembly 11 will transmit data to the computer system 15 indicative of contact. In response to the computer system 15 determining that the data received from the sensor assembly 11 is indicative of a contact between the distal tip 24 and a patient's body 14, the computer system 15 may operate a light-emitting-diode on the handle 21, a tone generator, a vibrating mechanical transducer, and/or other indicator(s), the outputs of which could vary in proportion to the calculated contact force.

The computer system 15 may utilize software, hardware, firmware, and/or logic to perform a number of functions described herein. The computer system 15 may be a combination of hardware and instructions to share information. The hardware, for example may include processing resource 16 and/or a memory 17 (e.g., non-transitory computer-readable medium (CRM) database, etc.). A processing resource 16, as used herein, may include a number of processors capable of executing instructions stored by the memory resource 17. Processing resource 16 may be integrated in a single device or distributed across multiple devices. The instructions (e.g., computer-readable instructions (CRI)) may include instructions stored on the memory 17 and executable by the processing resource 16 for force detection.

The memory resource 17 is communicatively coupled with the processing resource 16. A memory 17, as used herein, may include a number of memory components capable of storing instructions that are executed by processing resource 16. Such a memory 17 may be a non-transitory computer readable storage medium, for example. The memory 17 may be integrated in a single device or distributed across multiple devices. Further, the memory 17 may be fully or partially integrated in the same device as the processing resource 16 or it may be separate but accessible to that device and the processing resource 16. Thus, it is noted that the computer system 15 may be implemented on a user device and/or a collection of user devices, on a mobile device and/or a collection of mobile devices, and/or on a combination of the user devices and the mobile devices.

The memory 17 may be communicatively coupled with the processing resource 16 via a communication link (e.g., path). The communication link may be local or remote to a computing device associated with the processing resource 16. Examples of a local communication link may include an electronic bus internal to a computing device where the memory 17 is one of a volatile, non-volatile, fixed, and/or removable storage medium in communication with the processing resource 16 via the electronic bus.

In various embodiments of the present disclosure, the computer system 15 may receive optical signals from a sensor assembly 11 via one or more optical fibers extending a length of the catheter shaft 22. A processing resource 16 of the computer system 15 may execute an algorithm stored in memory 17 to compute a force exerted on distal tip 24, based on the received optical signals.

U.S. Pat. No. 8,567,265 discloses various optical force sensors for use in medical catheter applications, such optical force sensors are hereby incorporated by reference as though fully disclosed herein.

Figures 1A, 1B, 1C:
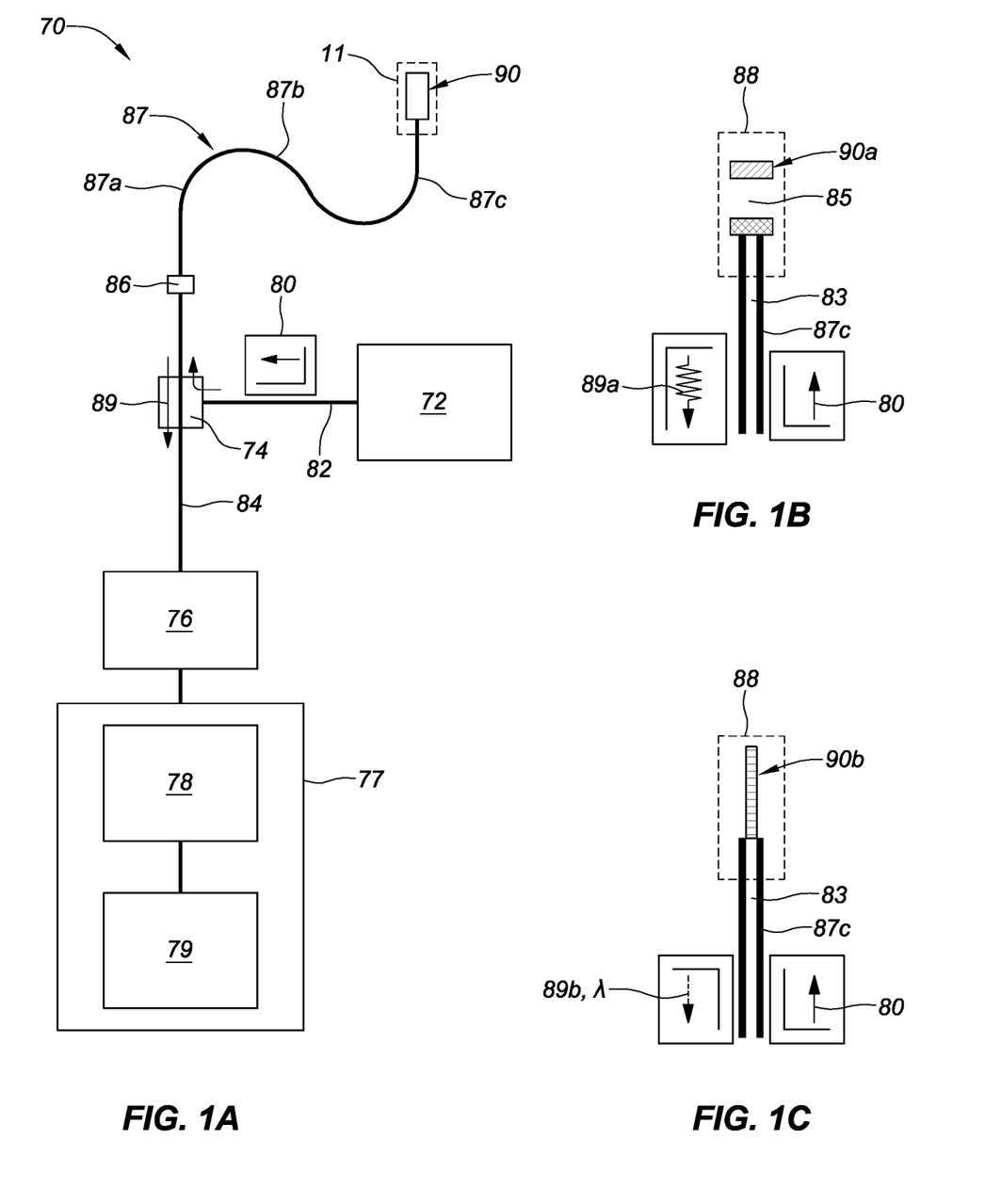
FIG. 1A is a block diagram of a force sensing system, consistent with various embodiments of the present disclosure.
FIG. 1B is a schematic depiction of an interferometric fiber optic sensor, consistent with various embodiments of the present disclosure.
FIG. 1C is a schematic depiction of a fiber Bragg grating optical strain sensor, consistent with various embodiments of the present disclosure.

FIG. 1A is a block diagram of a force sensing system 70, consistent with various embodiments of the present disclosure. The force sensing system 70 may comprise an electromagnetic source 72, a coupler 74, a receiver 76, an operator console 77 operatively coupled with a microprocessor 78 and a storage device 79. The electromagnetic source 72 transmits electromagnetic radiation 80 (photons) that is substantially steady state in nature, such as a laser or a broadband light source. A transmission line 82 such as a fiber optic cable carries the radiation 80 to the coupler 74, which directs the radiation 80 through a transmitting/receiving line 84 and through a fiber optic element contained within a flexible, elongated catheter assembly 87 to a fiber optic force sensing element 90 within a sensor assembly 11. It is to be understood that while various embodiments of the present disclosure are directed to sensing systems with fiber optic force sensing elements for detecting a change in dimension (e.g., deformation) of a catheter assembly 87, various other embodiments may include non-fiber optic based measurement systems as are well known in the art. Moreover, it is to be understood that the sensing elements measure the deformation of a deformable body (e.g., a distance or displacement), and do not directly measure a force. The catheter assembly 87 may include one or more transmitting/receiving lines 84 coupled to one or more fiber optic elements 83 (as shown in FIGS. 1B-C) within the sensor assembly 11. The fiber optic element(s) 83 of the catheter assembly 87 and transmitting/receiving(s) line 84 may be coupled through a connector 86 as depicted in FIG. 1A.

The catheter assembly 87 may have a width and a length suitable for insertion into a bodily vessel or organ. In one embodiment, the catheter assembly 87 comprises a proximal portion 87a, a middle portion 87b and a distal portion 87c. The distal portion 87c may include an end effector which may house the sensor assembly 11 and the one or more fiber optic sensing element(s) 90. The catheter assembly may be of a hollow construction (i.e. having a lumen) or of a non-hollow construction (i.e. no lumen), depending on the application.

In response to a deformation of a deformable body, due to a force being exerted on a distal tip of a catheter, one or more fiber optic elements 83 (as shown in FIGS. 1B-C) within the sensor assembly 11 will modulate the radiation received from the transmission line 82 and transmit the modulated radiation to the operator console 77 via receiving line 84. Once the radiation is received by the operator console 77, a microprocessor 78 may run an algorithm stored on storage device 79 to determine a distance across the sensing element(s) 90 and associate the distance with a force exerted on the catheter tip.

A fiber optic sensing element 90 for detecting a deformation of a deformable body may be an interferometric fiber optic strain sensor, a fiber Bragg grating strain sensor, or other fiber optic sensor well known in the art.

Referring to FIG. 1B, fiber optic sensing element 88 is an interferometric fiber optic strain sensor 90a. In this embodiment, the transmitted radiation 80 enters an interferometric gap 85 within the interferometric fiber optic strain sensor 90a. A portion of the radiation that enters the interferometric gap 85 is returned to the fiber optic cable 87c as a modulated waveform 89a. The various components of the interferometric fiber optic strain sensor 90 may comprise a structure that is integral with the fiber optic element 83. Alternatively, the fiber optic element 83 may cooperate with the structure to which it is mounted to form the interferometric gap 85.

Referring to FIG. 1C, fiber optic sensing element 90, of FIG. 1A, is a fiber Bragg grating strain sensor 90b. In this embodiment, the transmitted radiation 80 enters a fiber Bragg grating 90b, the gratings of which are typically integral with the fiber optic element 83 and reflect only a portion 89b of the transmitted radiation 80 about a central wavelength λ. The central wavelength λ at which the portion 89b is reflected is a function of the spacing between the gratings of the fiber Bragg grating. Therefore, the central wavelength λ is indicative of the strain on the fiber Bragg grating strain sensor 90b relative to some reference state.

The reflected radiation 89, be it the modulated waveform 89a (as in FIG. 1B) or the reflected portion 89b (as in FIG. 1C), is transmitted back through the transmitting/receiving line 84 to the receiver 76. The strain sensing system 70 may interrogate the one or more fiber optic strain sensing element(s) 90 at an exemplary and non-limiting rate of 10-Hz. The receiver 76 is selected to correspond with the type of strain sensing element 90 utilized. That is, the receiver may be selected to either detect the frequency of the modulated waveform 89a for use with the interferometric fiber optic strain sensor 90a, or to resolve the central wavelength of the reflected portion 89b for use with fiber Bragg grating strain sensor 90b. The receiver 76 manipulates and/or converts the incoming reflected radiation 89 into digital signals for processing by the microprocessor 78.

Figure 2A:
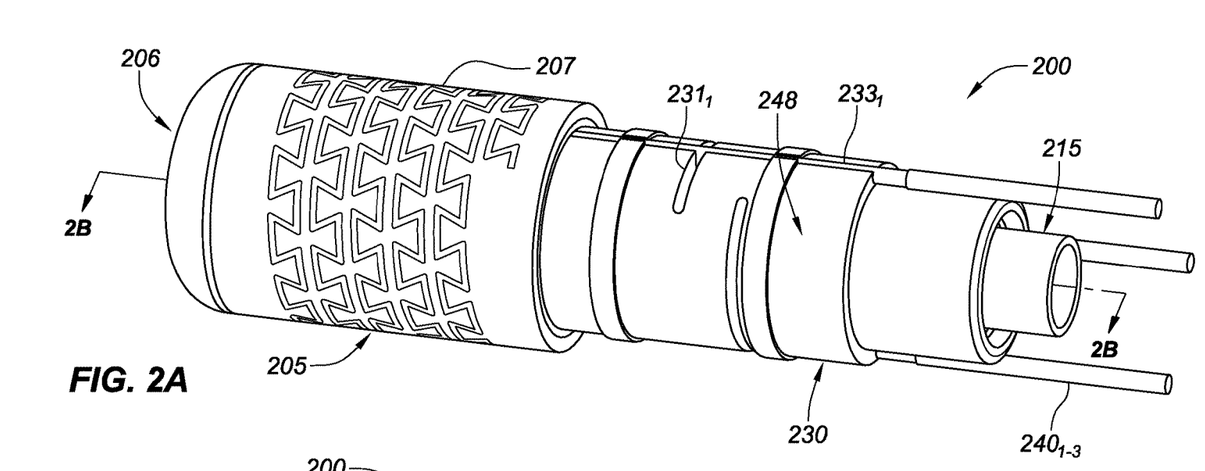
FIG. 2A is an isometric side view of a partial ablation catheter tip assembly including a deformable body, consistent with various embodiments of the present disclosure.
Figure 2B:
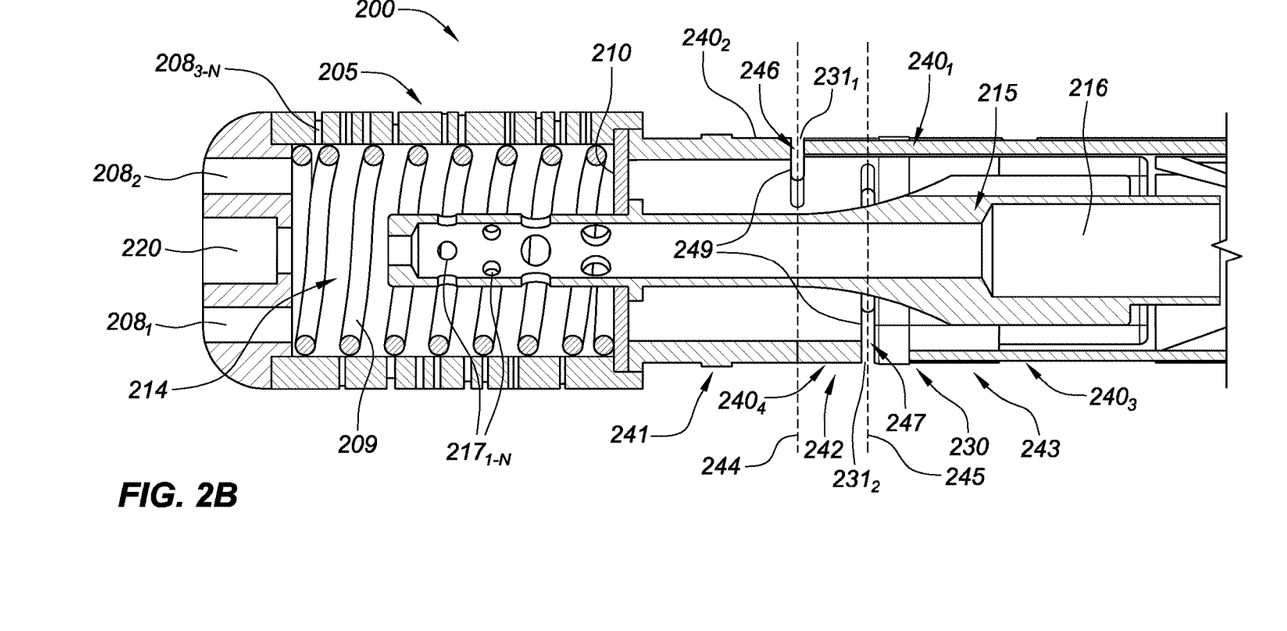
FIG. 2B is a cross-sectional side view of the partial ablation catheter tip assembly of FIG. 2A, consistent with various embodiments of the present disclosure.

FIG. 2A is an isometric side view of a partial ablation catheter tip assembly 200, FIG. 2B is a cross-sectional side view of the partial ablation catheter tip assembly of FIG. 2A, consistent with various embodiments of the present disclosure.

Referring to FIGS. 2A-B, partial ablation catheter tip assembly 200 includes a flex tip 205 that is coupled to a manifold 215 via a tip base 210. The tip base 210 may be comprised of, for example, a titanium alloy such as grades 2 or 9, or a stainless steel alloy such as 304 stainless steel or 316 stainless steel. The manifold 215 may be comprised of, for example, a stainless steel alloy, MP35N (a cobalt chrome alloy), titanium alloy, or a composition thereof. The flex tip 205 includes a distal tip 206 and a flexible member 207. The flexible member 207 facilitates deformation of the flex tip in response to contact with tissue; more specifically, the flexible member 207 deforms to increase surface contact with target tissue. The increased tissue surface contact improves outcomes for various diagnostics and therapies (e.g., tissue ablation). After contact with target tissue is complete, a spring 209 returns the flexible member 207 to an un-deformed state. The distal tip 206 may be coupled to the flexible member 207 via an adhesive, weld, etc. Similarly, the tip base 210 may be coupled to the flexible tip 205 via an adhesive, weld, etc. In some embodiments, the tip base 210 may be coupled to a distal portion of structural member 230 via an adhesive, weld, etc. A distal end of the manifold 215 extends through a lumen of the tip base 210 and inserted into a dispersion chamber 214 within the flex tip 205.

In various embodiments of the present disclosure, to limit the deformation of a structural member 230, partial ablation catheter tip assembly 200 may transmit a portion of a force exerted on flex tip 205 through a manifold 215 (bypassing structural member 230). The manifold 215 transmits the force to a catheter shaft that is coupled to a proximal end of the tip assembly 200. To facilitate large force loads on the manifold 215, the manifold may include a strain relief which limits lateral deflection of the manifold 215 in response to a force exerted on the tip assembly 200 transverse to a longitudinal axis.

Structural member 230, manifold 215, and tip base 210 comprise a deformable body of partial ablation catheter tip assembly 200.

Aspects of the present disclosure are further directed to solving the interdependency problem between axial and trans-axial compliance of a deformable body, which had previously prevented achieving a compliance ratio of 1:1 in a deformable body. As such, embodiments consistent with the present disclosure may decrease a perpendicular load compliance of the structural member 230 without causing a concomitant decrease in the axial load compliance. 1:1 compliance ratio of the deformable body may be achieved by distributing the bending moment of the applied force across two cross-sections separated by a distance. For example, the structural member 230 and manifold 215 (via tip base 210). As a result, the trans-axial/axial compliance ratio of deformable body may be tuned to substantially 1:1.

Manifold 215 includes an irrigant lumen 216 that delivers irrigant from a distal end of the catheter shaft to a dispersion chamber 214 within the flex tip 205 via manifold apertures $217_{1-N}$. The placement of the manifold apertures $217_{1-N}$ both along a length and circumference of a distal tip of the manifold 215 help facilitate even distribution of irrigant throughout the dispersion chamber 214. Once inside the dispersion chamber 214, the irrigant exits the flex tip 205 via irrigant apertures $208_{1-N}$, by virtue of positive pressure therein.

To measure real-time temperature of tissue in contact with a distal tip 206 of the tip assembly 200, it is desirable to position a thermocouple 220 as proximal to the tissue as possible. In the present embodiment, the thermocouple 220 is positioned so that a surface of the thermocouple 220 may be directly, thermally coupled to the tissue.

In some embodiments, a flexible member 207 of flex tip 205 may comprise a titanium alloy (or other metal alloy with characteristics including a high tensile strength).

Structural member 230 houses a plurality of fiber optic cables $240_{1-3}$ that extend through grooves, for example groove $233_1$. In the present embodiment, the structural member 230 is divided into a plurality of segments along a longitudinal axis. The segments 241, 242, 243 are bridged by flexure portions $231_{1-2}$, each flexure portion defining a neutral axes 244 and 245. Each of the neutral axes constitute a location within the respective flexure portions where the stress is zero when subjected to a pure bending moment in any direction.

In some embodiments, adjacent members of the segments 241, 242, and 243 may define a plurality of gaps 246 and 247 at the flexure portions $231_{1-2}$, each having a separation dimension. It is noted that while the longitudinal separation dimensions of the gaps are depicted as being uniform, the separation dimensions may vary across a given gap, or between gaps. Moreover, the radial dimension of the gaps may also vary (e.g., to compensate for the effects of a moment exerted along a length of the structural member 230).

Structural member 230 may include a plurality of grooves, for example groove $233_1$, that are formed within an outer surface 248 of the structural member. The grooves 233 may be spaced rotationally equidistant (i.e. spaced 90° apart where there are three grooves) about a longitudinal axis and may be oriented parallel with the longitudinal axis of the structural member 230. Each of the grooves may terminate at a respective one of the gaps 246 and 247 of the flexure portions $231_{1-2}$. For example, groove $233_1$ may extend along a proximal segment 243 and intermediate segment 242 terminating at the gap 246 at flexure portion $231_1$. Other grooves may extend along the proximal segment 243 terminating at the gap 247 at flexure portion $231_2$.

In a fiber optic distance measurement sensor, fiber optic cables $240_{1-3}$ may be disposed in grooves 233, respectively, such that the distal ends of the fiber optic cables terminate at the gaps 246 and 247 of either flexure portion $231_{1-2}$. For example, a first fiber optic cable $240_1$ may extend along groove $233_1$, terminating proximate or within the gap 246 at flexure portion $231_1$. Likewise, a second fiber optic cable $240_2$ may extend along a second groove 233 and terminate proximate or within the gap 247 at flexure portion $231_2$. Surfaces 249 of the flexure portions $231_{1-2}$, opposite the distal ends of first and second fiber optic cables, may be coated with a highly reflective material, or third and fourth fiber optics with mirrored surfaces positioned opposite the first and second fiber optics, relative to the gaps 246 and 247. Alternatively, a fiber Bragg grating strain sensor may be implemented.

Gaps 246 and 247 at flexure portions $231_{1-2}$ may be formed so that they extend laterally through a major portion of structural member 230. Also, the gaps may be oriented to extend substantially normal to a longitudinal axis of the structural member 230, or at an acute angle with respect to the longitudinal axis. In the depicted embodiment, the structural member 230 comprises a hollow cylindrical tube with the gaps 246 and 247 extending transverse to the longitudinal axis through one side of the structural member. As shown in FIGS. 2A, and 2B, flexure portions $231_{1-2}$ define a semi-circular segment that intercepts an inner diameter of structural member 230. The radial depth of the gaps 246 and 247 can be tuned to establish a desired flexibility of the various flexure portions $231_{1-2}$. That is, the greater the depth of the flexure portions $231_{1-2}$ the more flexible the flexure portions are. The flexure portions $231_{1-2}$ may be formed by the various ways available to the artisan, such as but not limited to sawing, laser cutting or electro-discharge machining (EDM). The gaps 246 and 247 which form the flexure portions $231_{1-2}$ may be formed to define non-coincident neutral axes.

When a fiber optic sensor consistent with the above is assembled, one or more fiber optic cables are mechanically coupled to structural member 230 via grooves 233. In some embodiments, each of the fiber optics may be communicatively coupled to a Fabry-Perot strain sensor within one of the gaps 246 and 247 which form the flexure portions $231_{1-2}$. The Fabry-Perot strain sensor includes transmitting and reflecting elements on either side of the slots to define an interferometric gap. The free end of the transmitting element may be faced with a semi-reflecting surface, and the free end of the reflecting element may be faced with a semi-reflecting surface.

In some assemblies of a fiber optic sensor, the fiber optic cables may be positioned along the grooves $233_{1-3}$ (as shown in FIG. 2A) so that the respective Fabry-Perot strain sensor is bridged across one of the flexure portions $231_{1-2}$. For example, a fiber optic cable may be positioned within groove $233_1$ so that the Fabry-Perot strain sensor bridges the gap at the flexure portion $231_1$ between distal and intermediate segments, 241 and 242, respectively, of structural member 230.

In some embodiments, structural member 230 may comprise a composition including a stainless steel alloy (or other metal alloy with characteristics including a high tensile strength, e.g., titanium).

In response to a force exerted on a distal tip 206, structural member 230 deforms. The amount structural member 230 deforms is directly correlated to a force exerted on a distal tip 206. By tuning the dimensions of the structural member 230, tip base 210, and/or manifold 215, a desired compliance ratio of the deformable body system can be achieved. For example, it can be desirable to reduce a compliance of the structural member in response to trans-axial forces exerted on the distal tip 206 relative to a compliance of the structural member in response to an axial force exerted on the distal tip. By reducing the compliance of the structural member in response to trans-axial forces, without further stiffening the structural member to axial forces, the structural member may achieve a compliance ratio of (approximately) 1:1 between axial and radial deformation. As a result, the force determination complexity is greatly reduced as a deformation measurement, A, associated with a trans-axial contact with a force of B, will have the same deformation, A, as an axial contact with a force of B.

In partial ablation catheter tip assembly 200 of FIGS. 2A and 2B, a trans-axial compliance of structural member 230 is corrected by directing a portion of a force exerted on distal tip 206, through tip base 210, into manifold 215 which exhibits improved deformation characteristics in response to trans-axial loading. By re-directing a portion of the trans-axial load onto the manifold 215, the resulting trans-axial deformation of the structural member 230 is reduced. In various embodiments of the present disclosure, the tip base 210 may exhibit high deformation in response to axial force and reduced deformation in response to trans-axial forces. As a result, the tip base 210 (in conjunction with the manifold 215) will minimally increase the stiffness of the catheter tip assembly 200 in response to an axial force, while greatly increasing the stiffness in response to a trans-axial force. In some embodiments, the catheter tip assembly 200 may be tuned to (nearly) achieve a 1:1 compliance ratio.

Ablation catheter systems, including a structural member 230 for measuring forces exerted on an ablation tip, are susceptible to excess-force events prior and during use. These excess-force events may lead to permanent yielding of components within the deformable body including structural member 230, where the force exerted across the deformable body exceeds the maximum operating force. The maximum operating force is typically related to yield strengths of the components of the deformable body. Such excess-force events can occur, for example, during handling of the ablation catheter, during insertion of the ablation catheter into an introducer sheath, or due to excessively forceful steering of the ablation catheter within the cardiac muscle. When these excess-force events occur, the yielding of one or more portions of the deformable body change the system dynamics of the force sensor. Importantly, the calibrated correlation between a deformation measurement of the structural member and an associated force exerted on catheter tip 206 may no longer be accurate.

To prevent damage to a structural member 230 due to excess-force events, some embodiments of the present disclosure utilize deformation limiters. The deformation limiters prevent the deformable body from deforming to a yielding point, where the calibration between the deformation and the associated force exerted on a catheter tip is no longer accurate. The embodiment disclosed in FIGS. 2A-B addresses this challenge by utilizing manifold 215 as a trans-axial deformation limiter. Where the trans-axially exerted force (relative to a length of the deformable body) exceeds a maximum operating force of the structural member 230, an inner diameter of the deformed structural member comes into contact with, and is structurally supported by, an outer diameter of the manifold 215 to prevent the structural member from yielding under the excessive force.

Figure 2C:
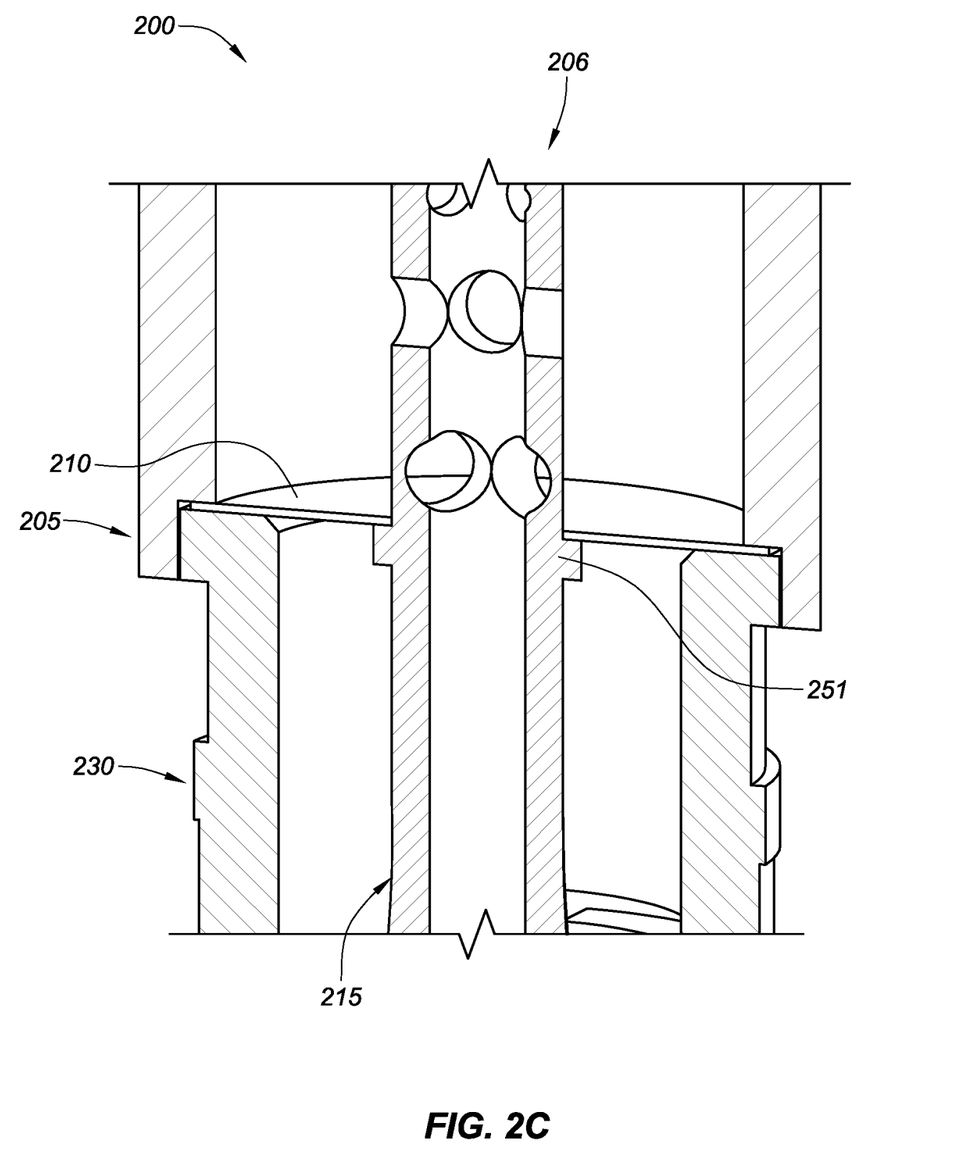
FIG. 2C is a close-up, cross-sectional side view of the partial ablation catheter tip assembly of FIG. 2A, consistent with various embodiments of the present disclosure.

Further referring to FIGS. 2A-C, a partial ablation catheter tip assembly 200 includes a structural member 230. The structural member 230 may be coupled at a distal end to tip base 210, and at a proximal end to manifold 215. Once the tip assembly 200 is complete, the structural member may be further coupled at a proximal end to a catheter shaft that extends to a catheter handle. The structural member 230 is designed in such a way as to receive forces exerted on the distal tip 206 of the catheter tip assembly 200 and to absorb such force by deflecting and deforming in response thereto. Further, the structural member 230 may be outfitted with a measurement device which facilitates measurement of the deflection/deformation which may be correlated with the force exerted on the distal tip 206 and communicated with a clinician. Knowledge of a force exerted on the distal tip 206 of a catheter may be useful for a number of different cardiovascular operations; for example, during a myocardial tissue ablation therapy it is desirable to know a contact force exerted by the distal tip 206 of the catheter on target tissue as the time to necrose tissue is based on energy transferred between the catheter and tissue—which is highly dependent upon the extent of tissue contact.

As shown in FIGS. 2A and 2B, partial ablation catheter tip assembly 200 utilizes a fiber optic based measurement system. Fiber optic cables $240_{1-4}$ are coupled to grooves (including groove $233_1$) along an outer diameter of structural member 230. Accordingly, a light source may be applied to one or more of the fiber optic cables and a time-of-flight measurement may be recorded for one or more wave-lengths of light to cross a gap between the fiber-optic pairs in flexure portions $231_{1-2}$. In various embodiments, the fiber optic cables run proximally along a shaft to a catheter handle, which may include processor circuitry or be communicatively coupled to the processor circuitry. The sensed time-of-flight across the flexure portions $231_{1-2}$ may be associated with a deflection of the deformable body from a static distance across the flexure portions. During calibration, the structural member 230 may be tested to determine a calibration matrix which associates deformation of the structural member with an applied-force at distal tip 206. Where the fiber optic based measurement system is a Fabry-Perot sensor, a phase change of light extending across the gap is indicative of a deformation of the deformable body.

As shown in FIG. 2B, tip base 210 is seated to and coupled with an inner diameter of structural member 230 at a proximal end, and is seated to and coupled with an inner diameter of flex tip 205 at a distal end. The tip base structurally transmits a force exerted on the flex tip 205 to both structural member 230 and manifold 215. By diverting a portion of the force exerted to the manifold, the tip assembly 200 as a whole exhibits improved stiffness especially in response to lateral deflection. In some embodiments, the manifold may absorb up to 50%, or more, of the force exerted on the distal tip. Moreover, in some more specific embodiments, the structural member 230 has an increased inner diameter and outer diameter, with pivot points of the flexure portions 231 being extended radially outward. Accordingly, the structural member 230 is stiffer and receives less of the force exerted on the distal tip 206, resulting in the structural member 230 experiencing less deflection and being less susceptible to plastic deformation during delivery of the catheter to a therapy site (e.g., via introducer sheath). Moreover, by transmitting force onto the manifold 215, the structural member 230 may be tuned to improve the compliance ratio of lateral-to-axial deflection.

Due to the tuning of deformable body, including structural member 230, tip base 210, and manifold 215, the deformation of the deformable body will be the same for a given exerted force (or resultant force of multiple force vectors), regardless of the directionality of a force being exerted on an ablation catheter tip assembly 200. This is particularly useful as this simplifies the correlation between a force exerted on the ablation catheter tip assembly 200 and a measured deformation at the deformable body. Given a tuned deformable body with a trans-axial/axial compliance ratio of 1:1, the deformation of the deformable body is directly associated with a force exerted upon the ablation catheter tip, and is independent of the force's vector. The association between deformation and force may be determined (learned) and stored in a lookup table for reference in response to deformation measurement of structural member 230. In yet other embodiments, the measured deformation may be input into an algorithm associated with the structural characteristics of the deformable body to determine the force and directionality at the catheter tip. During an ablation therapy procedure, a measurement device may determine the deformation of one or more of the flexure portions $231_{1-2}$ relative to a static-position, and utilize the look-up table to determine the amount of force the ablation catheter tip is experiencing. Without a trans-axial/axial compliance ratio near 1:1, the relationship between a force exerted upon the ablation catheter tip and a deformation of the deformable body becomes dependent on the directionality of the exerted force, or a resultant force of a number of forces exerted simultaneously. In one example embodiment, the resultant force is a vector sum of one or more force vectors exerted on the catheter tip.

Tuning a trans-axial/axial compliance ratio of a deformable body to near 1:1 is desirable as higher compliance ratios may result in dimensional clearance related issues with the catheter. For example, where the trans-axial compliance relative to the axial compliance is too high (e.g., 100:1), the minimum level of axial deflection required for a given measurement system to detect the axial deflection (or have a desired application-specific sensitivity) requires a trans-axial deflection that is the axial compliance multiplied by the compliance ratio of the deformable body. In such a case, the trans-axial deflection can become an unfeasibly large portion of a diameter of the catheter shaft, which may limit space for lead wires, irrigant lumens, etc. which traverse through the deformable body. Moreover, in many applications the protective materials/coatings applied to an exterior of the ablation catheter tip may have limited elasticity which can be exceeded by a deformable body that allows for large lateral compliance of the ablation catheter tip 200.

It is to be understood that the material characteristics and the dimensions of structural member 230, tip base 210, and manifold 215 may be calibrated to optimize the movement of the system in response to an expected range of forces exerted on a distal tip 206 for a given medical application. Alternatively, the deformable body may be calibrated to suit the specifications of a magnetic sensor-based deformation measurement system. For example, where the magnetic sensor has a resolution for detecting movement of a magnet of 0.1 millimeters, the material characteristics and dimensional characteristics for the deformable body may be selected for a given range of application forces (e.g., forces exerted on the distal tip 206 between 0-10 grams) that allows total use of the sensor resolution range. Similarly, the length of the structural member 230 may be selected in accordance with the off-axis sensor resolution and the angular off-axis displacement of the deformable body in response to a given range of trans-axial forces applied on the distal tip 206.

FIG. 2C is a close-up, cross-sectional side view of partial ablation catheter tip assembly 200 of FIG. 2A, consistent with various embodiments of the present disclosure. In FIG. 2C, a distal tip 206 of the assembly 200 is experiencing a force exerted laterally relative to a longitudinal axis of the catheter shaft. The force is transmitted proximally down the assembly 200 along both structural member 230 and manifold 215 via tip base 210. Due to the shape and material characteristics of tip base 210, lateral forces are transmitted to the manifold 215 with minimal deformation of the tip base 210. As a result, a large portion of the lateral forces may be carried by the manifold 215—reducing the compliance of the structural member in response to lateral forces.

In response to a lateral force exerted on a distal tip of the assembly 200, flexible tip 205 transmits the force to an outer diameter of tip base 210 and structural member 230. The structural member 230 is placed into a combination of tension and compression in response to the force which causes the deformation at flexure portions 231 which may be measured to determine a magnitude and directionality of the force exerted. The outer diameter of tip base 210 transmits a portion of the force to an outer diameter of manifold 215, which is mechanically coupled to an inner diameter of the tip base 210. In various embodiments, the manifold may be comprised of a material that will minimally deform in response to the types of forces experienced during an intravascular catheter operation.

Tip base 210 of the ablation catheter tip assembly 200 may be held within the assembly by a compression fit between flexible tip 205 and structural member 230. In some embodiments, the joint between the flexible tip 205 and the structural member 230 may be laser welded (or otherwise coupled) circumferentially about an outer diameter of the flexible tip. Where the tip base 210 material is compatible, it may also be desirable to weld the tip base with the flexible tip 205 and the structural member 230. An inner diameter of the tip base 210 is further assembled about an outer diameter of manifold 215. In some embodiments, a protrusion 251 may facilitate positive longitudinal placement of the manifold 215 relative to the rest of the ablation catheter tip assembly 200. In further embodiments, the tip base 210 may be laser welded (or otherwise coupled) to the manifold 215.

Figure 2D:
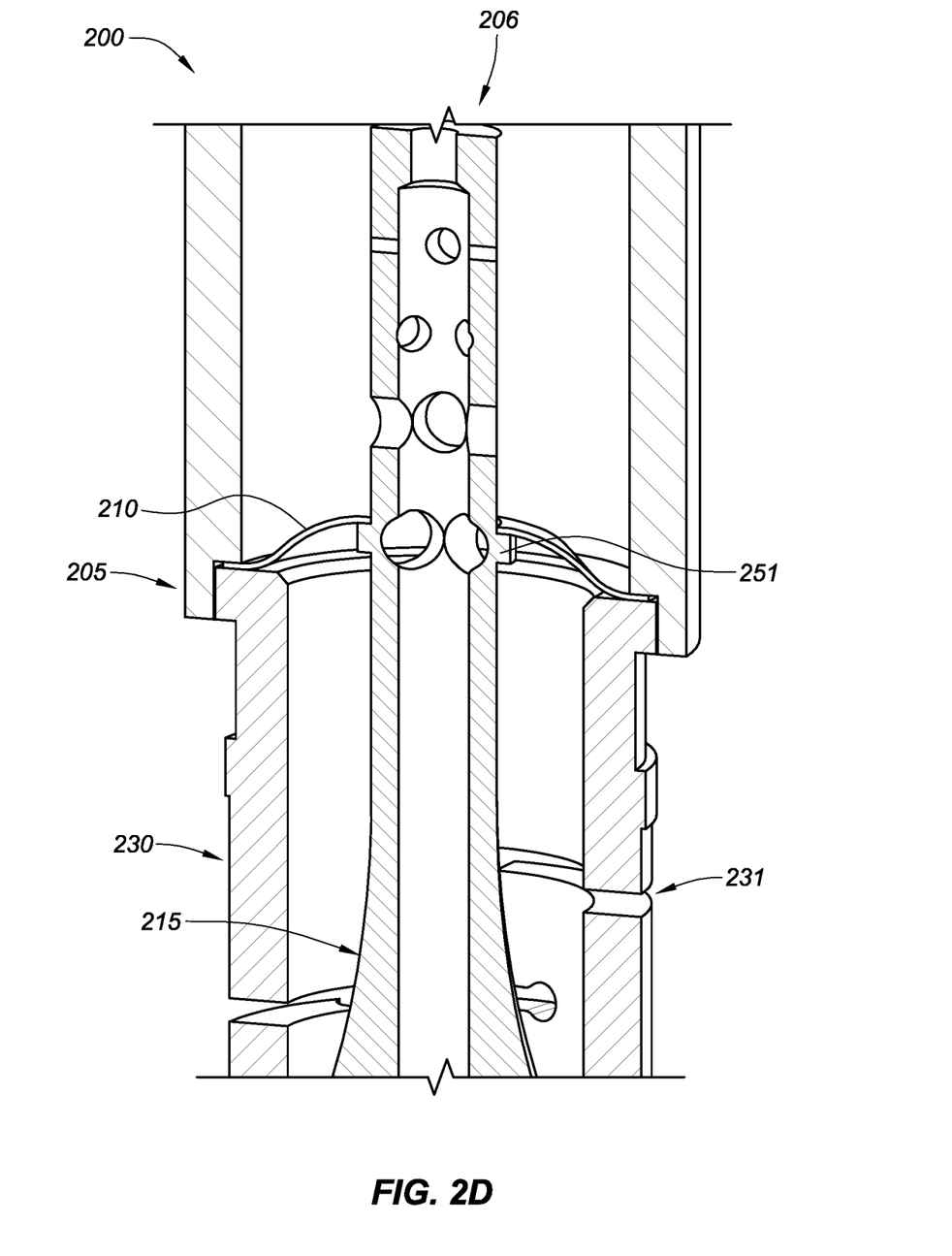
FIG. 2D is a close-up, cross-sectional side view of the partial ablation catheter tip assembly of FIG. 2A, consistent with various embodiments of the present disclosure.

FIG. 2D is a close-up, cross-sectional side view of the partial ablation catheter tip assembly 200 of FIG. 2A, consistent with various embodiments of the present disclosure. In FIG. 2D, a distal tip 206 of the assembly 200 is experiencing a force exerted axially relative to a longitudinal axis of the catheter shaft. The force is transmitted proximally down the assembly 200 along both structural member 230 and manifold 215 via tip base 210. Due to the shape and material characteristics of tip base 210, axial forces are minimally transmitted to the manifold 215 due to a large deformation of the tip base 210. As a result, a majority of the axial forces are carried by the structural member 230—maintaining a compliance of the deformable body in response to axial forces.

In response to an axial force exerted on distal tip 206 of the assembly 200, flexible tip 205 transmits the force to an outer diameter of tip base 210 and structural member 230. The structural member 230 is placed into compression in response to the axial force which causes the deformation at flexure portions 231 which may be measured to determine a magnitude of the force exerted. Due to the deformation of the tip base 210 in response to the axially exerted force, little force is transmitted to the manifold 215. The large axial compliance of the tip base 210, as compared to its minimal lateral compliance, is due to the thin annular shape of the tip base. To further facilitate the desirable characteristics of the tip base 210, the tip base may be comprised of a material with uni-directional strength characteristics.

As shown in FIG. 2D, the axial force exerted on distal tip 206 causes relative motion between the manifold 215 and the remainder of assembly 200. A protrusion 251 extends circumferentially about an outer diameter of the manifold 215, and maintains a longitudinal position of the coupling joint between the manifold and a tip base 210. An axial force exerted on the distal tip 206 causes a deformation of the tip base 210 due to the change in relative positioning of the manifold 215 and the remainder of assembly 200.

Figure 3:
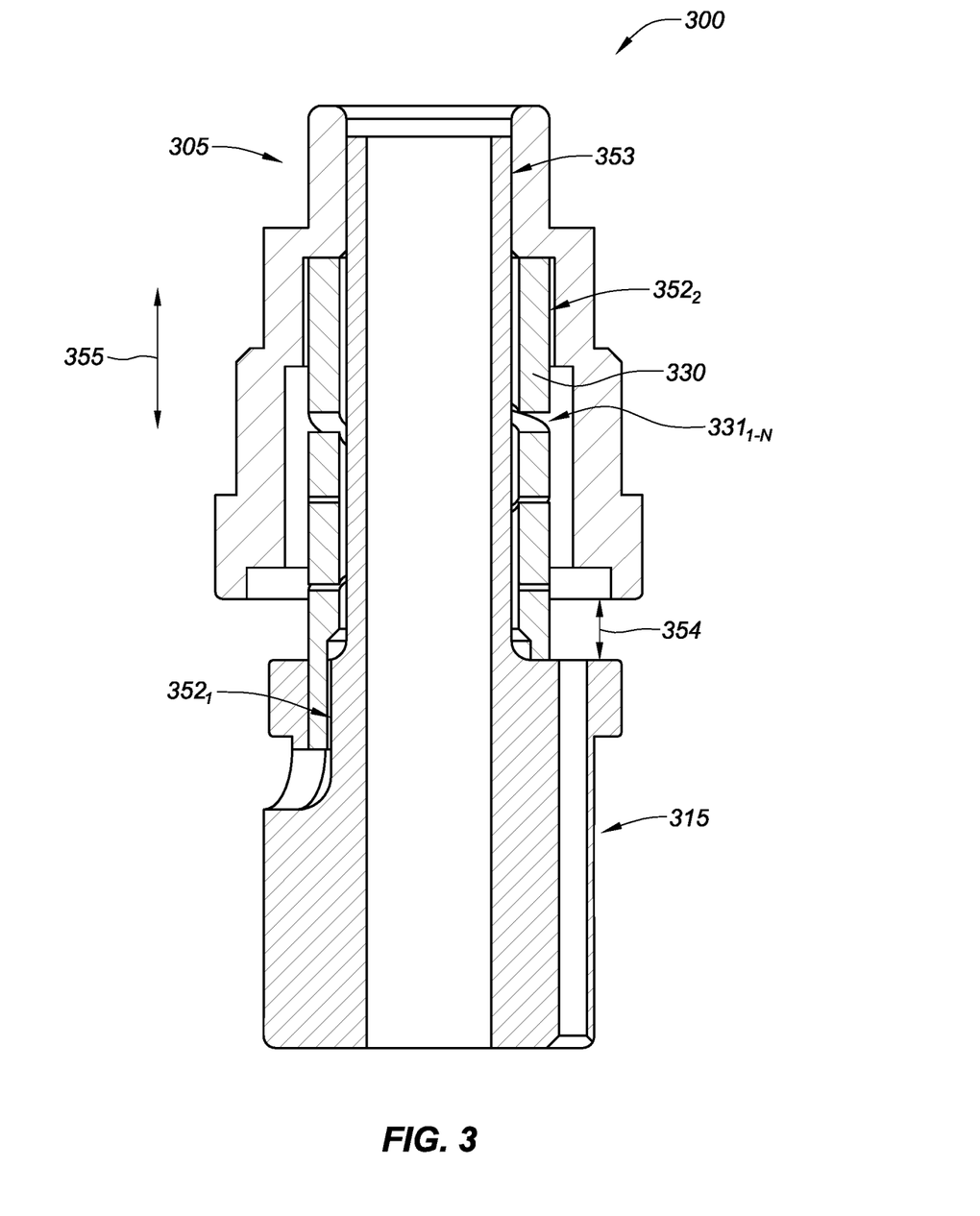
FIG. 3 is a cross-sectional side view of a deformable body assembly for an electrophysiology catheter, consistent with various embodiments of the present disclosure.

FIG. 3 is a cross-sectional side view of a deformable body assembly 300 for an electrophysiology catheter, consistent with various embodiments of the present disclosure. The deformable body assembly 300 of FIG. 3 facilitates independent axial and lateral stiffness. While stiffness independence, consistent with the present embodiment, may be achieved with as few as one part using newer manufacturing methods such as additive manufacturing, simpler implementations may use multiple parts manufactured using more traditional manufacturing techniques (e.g., machining, molding, etc.).

As shown in FIG. 3, a proximal body 315 is welded (or otherwise coupled) to axial spring 330 at a proximal end thereof. The weld $352_1$ may extend circumferentially between the proximal body 315 and the axial spring 330. The axial spring 330 is further welded to tip adapter 305 at a distal end of the axial spring. The weld $352_2$ may extend circumferentially between the tip adapter 305 and the axial spring 330.

A deformable body assembly 300 may be used in conjunction with a force sensor that utilizes a measurement system to determine a relative motion 355 between tip adapter 305 and proximal body 315. In such an embodiment, the determined deflection 354 may be compared with a calibration matrix to calculate a force exerted on a catheter tip. Material and shape selection (e.g., inner diameter, outer diameter, flexure portions $331_{1-N}$ dimensions, etc.) of axial spring 330 facilitates independent adjustment of the axial stiffness of deformable body 300. Material and shape selection (e.g., inner diameter, outer diameter, etc.) of proximal body 315 facilitates independent adjustment of the lateral stiffness of deformable body 300. A slip fit/sliding interface 353 may be desirable between the distal end of proximal body 315 and tip adapter 305 to facilitate axial travel of the tip adapter. The sliding interface 353 facilitates relative motion 355 of tip adapter 305 relative to proximal body 315 in response to an axial force. The axial spring 330 deflects in response to an axial load placed on the tip adapter 305. In some embodiments, it may be desirable to prevent rotation of the tip adapter relative to the proximal body. In such embodiments, the tip adapter and proximal body may have non-cylindrical cross-sections (e.g., triangular, rectangular, etc.).

The deformable body assembly 300 may be further coupled into a complete electrophysiology catheter assembly. In the final assembly, a distal tip of the catheter may be welded to tip adapter 305 and proximal body 315 is welded to a catheter shaft.

Figure 4A:
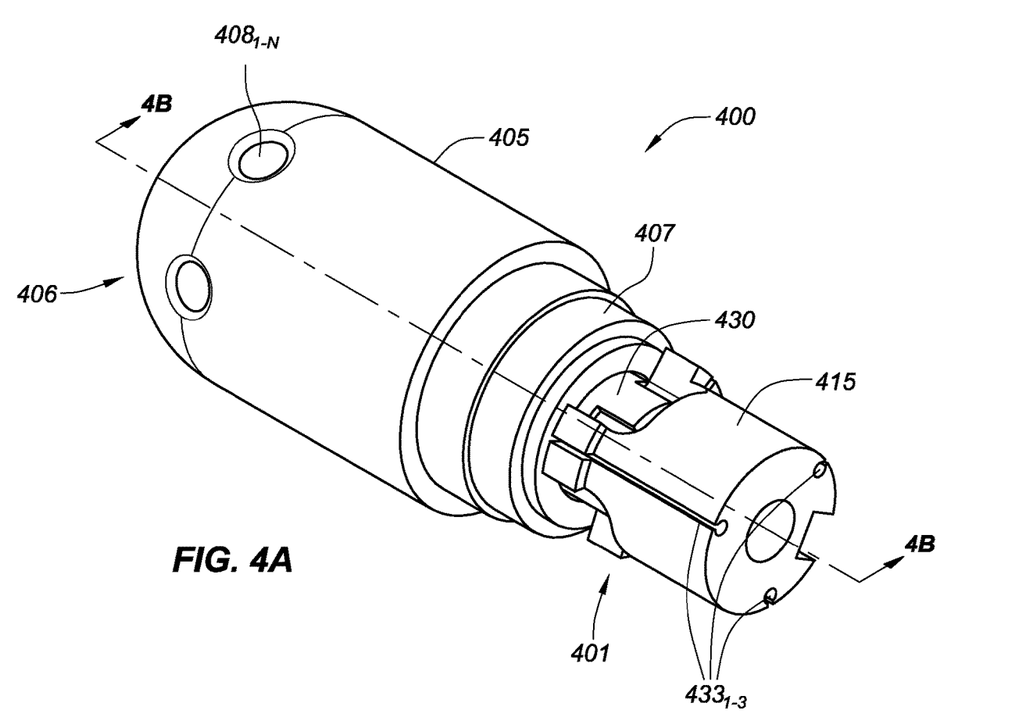
FIG. 4A is an isometric side view of a partial ablation catheter tip assembly including a deformable body, consistent with various embodiments of the present disclosure.
Figure 4B:
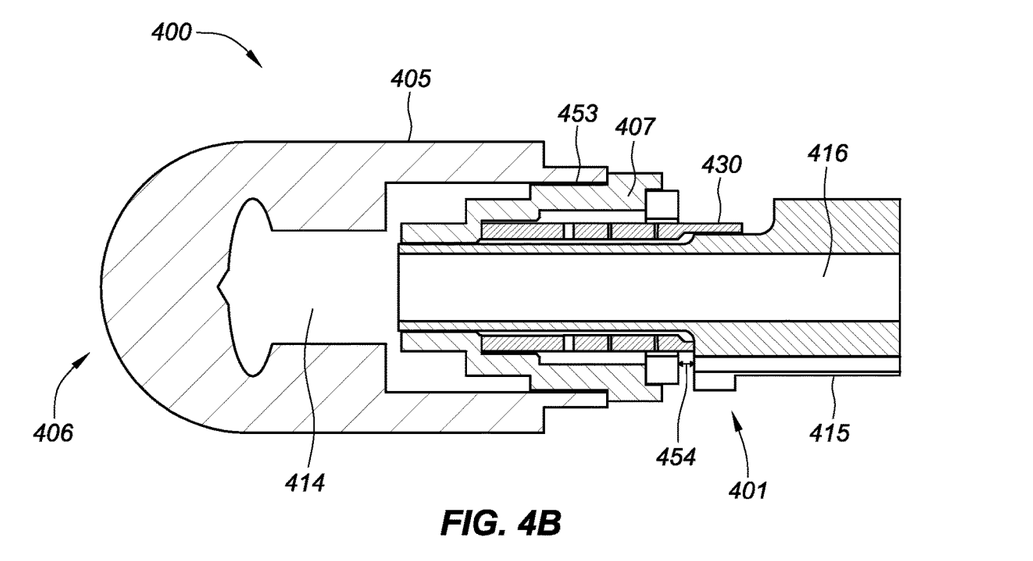
FIG. 4B is a cross-sectional side view of the partial ablation catheter tip assembly of FIG. 4A, consistent with various embodiments of the present disclosure.

FIG. 4A is an isometric side view of a partial ablation catheter tip assembly 400 including a deformable body, and FIG. 4B is a cross-sectional side view of the partial ablation catheter tip assembly 400 of FIG. 4A. The partial ablation catheter tip assembly 400 utilizes a fiber optic based measurement system. Fiber optic cables are coupled to grooves $433_{1-3}$ along an outer surface of a proximal body 415. A deformable body assembly 401 includes the proximal body 415, an axial spring 430 that is welded to a proximal end of proximal body 415, and a tip adapter 407. The weld may extend circumferentially between the proximal body 415 and the axial spring 430. The axial spring 430 is further welded to the tip adapter 407 at a distal end of the axial spring.

The fiber optic based measurement system applies a light source to the one or more fiber optic cables and a time-of-flight measurement may be recorded for one or more wavelengths of light to cross a gap 454 (as shown in FIG. 4B). In various embodiments, the fiber optic cables run proximally along a shaft to a catheter handle, which may include processor circuitry or be communicatively coupled to the processor circuitry. The sensed time-of-flight across the gap may be associated with a deflection of the deformable body from a static distance. During calibration, the deformable body assembly 401 may be tested to determine a calibration matrix which associates deformation of the deformable body assembly with an applied-force at distal tip 406. Where the fiber optic based measurement system is Fabry-Perot sensor, a phase change of light extending across the gap is indicative of a deformation of the deformable body.

As shown in FIG. 4A, partial ablation catheter tip assembly 400 includes an irrigation lumen 416 which extends up through deformable body assembly 401 and delivers irrigant to dispersion chamber 414 (as shown in FIG. 4B). The irrigant exits tip 405 via irrigant apertures $408_{1-N}$, by virtue of positive pressure therein.

As shown in FIG. 4B, a proximal portion of tip 405 is seated to and coupled with a distal end of adaptor 407. The tip 405 structurally transmits a force exerted on a distal end 406 through adaptor 407 and axial spring 430 to proximal body 415.

A deformable body assembly 401 may be used in conjunction with a force sensor that utilizes a measurement system to determine a relative motion between tip adapter 407 and proximal body 415. In such an embodiment, the determined deflection across the gap 454 may be compared with a calibration matrix to calculate a force exerted on catheter tip 405. A slip fit/sliding interface 453 may be desirable between a distal end of proximal body 415 and tip adapter 407 to facilitate axial travel of the tip adapter. The sliding interface 453 facilitates relative motion of tip adapter 407 relative to proximal body 415 in response to an axial force. The axial spring 430 deflects in response to an axial load placed on the tip adapter 407.

In response to a lateral force on the catheter tip 405, the force is transferred through the adaptor 407 to proximal body 415, with very little lateral force being exerted on the axial spring 430. By handling lateral and axial forces differently, deformable body assembly 401 may be tuned to achieve a desired axial to lateral compliance ratio of the deformable body.

As shown in FIGS. 4A-B, deformable body assembly 401 may be further coupled into a partial ablation catheter tip assembly 400. In the final assembly, a tip 405 of the catheter may be welded to tip adapter 407 and proximal body 415 may be welded to a catheter shaft (not shown).

While various embodiments of the present disclosure are discussed in reference to an ablation catheter, it is to be understood that a catheter consistent with the present disclosure may implement various different types of end effectors—e.g., mapping electrodes or ablation electrodes, such as are known in the art for diagnosis or treatment of a vessel or organ may be utilized with the present invention. For example, the catheter tip assembly may be configured as an electrophysiology catheter for performing cardiac mapping. In other embodiments, the catheter tip assembly may be configured to deliver drugs or bioactive agents to a vessel or organ wall or to perform minimally invasive procedures.

U.S. provisional application No. 62/331,292, filed 3 May 2016, U.S. application Ser. No. 15/585,859, filed 3 May 2017, international application no. PCT/US17/30828, filed 3 May 2017, U.S. provisional application No. 62/455,048, filed 6 Feb. 2017, U.S. provisional application No. 62/541,805, filed 7 Aug. 2017, and U.S. provisional application No. 62/540,409, filed 2 Aug. 2017, are all hereby incorporated by reference as though fully set forth herein.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Although process steps, method steps, algorithms, or the like, can be described in a sequential order, such processes, methods, and algorithms can be configured to work in alternative orders. In other words, any sequence or order of steps that can be described does not necessarily indicate a requirement that the steps be performed in that order. The steps of the processes, methods, and algorithms described herein can be performed in any order practical. Further, some steps can be performed simultaneously.

When a single device or article is described herein, it will be readily apparent that more than one device or article can be used in place of a single device or article. Similarly, where more than one device or article is described herein, it will be readily apparent that a single device or article can be used in place of the more than one device or article. The functionality or the features of a device can be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Various modules or other circuits can be implemented to carry out one or more of the operations and activities described herein and/or shown in the figures. In these contexts, a "module" is a circuit that carries out one or more of these or related operations/activities (e.g., processor circuitry). For example, in certain of the above-discussed embodiments, one or more modules are discrete logic circuits or programmable logic circuits configured and arranged for implementing these operations/activities. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A force-sensing catheter system comprising:
    a catheter tip including a flexible member and a spring coupled to the flexible member; and
    a deformable body including:
        a structural member coupled to the catheter tip and including a lumen that extends along a longitudinal axis of the force-sensing catheter system, the structural member is configured and arranged to deform in response to a force exerted on the catheter tip, and
        a manifold that extends through the lumen of the structural member, the manifold coupled to the catheter tip and a proximal end of the structural member, the manifold configured and arranged to proximally transmit a portion of the force exerted on the catheter tip bypassing the structural member,
    wherein the force exerted on the catheter tip causes the flexible member to deform to increase surface contact with contacted tissue, and wherein the spring causes the flexible member to return to an undeformed state when the force exerted on the catheter tip is removed.

2. The force-sensing catheter system of claim 1, wherein the deformable body further includes a tip base coupling the catheter tip to the manifold, the tip base having an annular shape with inner and outer surfaces, the outer surface is circumferentially coupled to a distal end of the structural member and the inner surface is circumferentially coupled to the manifold, the tip base is configured to transmit a portion of the force exerted on the catheter tip to the manifold.

3. The force-sensing catheter system of claim 2, wherein the tip base is further configured and arranged to transmit a lateral component of the force exerted on the catheter tip to the manifold, and to deform in response to an axial component of the force, thereby minimally transmitting the axial component to the manifold.

4. The force-sensing catheter system of claim 1, wherein the deformable body has a lateral-to-axial compliance ratio between 5:1 and 1:1.

5. The force-sensing catheter system of claim 1, wherein the manifold is further configured and arranged to deliver irrigant to the distal tip; and further including a dispersion chamber, within the catheter tip, configured and arranged to receive irrigant from the manifold and disburse the irrigant to an outer surface of the distal tip.

6. The force-sensing catheter system of claim 1, further including:
    a measurement system coupled to the structural member, the measurement system including three or more sensing elements, the sensing elements configured and arranged to detect the deformation of the structural member, in response to the force exerted on the catheter tip, and transmit a signal indicative of the deformation; and processor circuitry communicatively coupled to the measurement system, and configured and arranged to receive the signal from each of the sensing elements, indicative of the deformation, and to determine a magnitude of the force exerted on the catheter.

7. The force-sensing catheter system of claim 6, wherein the sensing elements are optical fibers, and the signal indicative of the deformation are photons.

8. The force-sensing catheter system of claim 6, wherein the sensing elements are Fabry-Perot interferometers, and wherein the processing circuitry is further configured and arranged to determine the force exerted on the catheter tip based on the interference pattern of light between two semi-reflective surfaces of the Fabry-Perot interferometer.

9. The force-sensing catheter system of claim 6, wherein the sensing elements are circumferentially distributed about the longitudinal axis of the force-sensing catheter system.

10. The force-sensing catheter system of claim 6, further including a display communicatively coupled to the processor circuitry, wherein the processor circuitry is further configured and arranged to transmit data to the display indicative of the force exerted on the catheter tip, and the display is configured and arranged to visually communicate the force to a clinician.

11. An ablation catheter tip assembly comprising:
a distal tip configured and arranged to deliver energy to contacted tissue;
a flexible member configured to deform to increase surface contact with the contacted tissue in response to a force exerted on the distal tip;
a spring coupled to the flexible member and configured to cause the flexible member to return to an undeformed state when the force exerted on the distal tip is removed; and
a deformable body mechanically coupled to a proximal end of the distal tip, the deformable body including:
  a structural member configured and arranged to deform in response to the force exerted on the distal tip, the structural member including a lumen that extends along a longitudinal axis of the ablation catheter tip assembly, and
  a manifold extends through the lumen of the structural member and is mechanically coupled to the proximal end of the distal tip, the manifold configured and arranged to limit deformation of the structural member in response to the force exerted on the distal tip by absorbing a portion of the force.

12. The ablation catheter tip assembly of claim 11, wherein the deformable body further includes a tip base having an annular shape with inner and outer surfaces, the outer surface is circumferentially coupled to the structural member and the inner surface is circumferentially coupled to the manifold, the tip base is configured to transmit a portion of the force exerted on the catheter tip to the manifold.

13. The ablation catheter tip assembly of claim 11, further including a measurement system coupled to the structural member, the measurement system including three or more sensing elements configured and arranged to detect the deformation of the structural member in response to the force exerted on the catheter tip and transmit a signal indicative of the deformation.

14. The ablation catheter tip assembly of claim 11, wherein the deformable body is further configured and arranged to emulate a desired lateral-to-axial compliance ratio by transmitting more or less of the force exerted on the catheter tip through the manifold.

* * * * *